US005698427A

United States Patent [19]

Keene et al.

[11] Patent Number: 5,698,427

[45] Date of Patent: Dec. 16, 1997

[54] METHODS AND COMPOSITIONS INVOLVED IN CELL GROWTH, NEOPLASIA AND IMMUNOREGULATION

[75] Inventors: Jack D. Keene; Peter H. King; Todd Levine, all of c/o Duke University, Durham, N.C. 27710

[73] Assignees: Jack D. Keene, Durham, N.C.; Peter H. King, Birmingham, Ala.; Todd Levine, Durham, N.C.

[21] Appl. No.: 470,469

[22] Filed: Jun. 6, 1995

Related U.S. Application Data

[62] Division of Ser. No. 881,075, May 11, 1992, Pat. No. 5,444,149.

[51] Int. Cl.[6] ........................ C12N 15/00; C07K 14/00

[52] U.S. Cl. ........................ 435/172.3; 530/350

[58] Field of Search ........................ 514/44; 435/172.3

[56] References Cited

PUBLICATIONS

Malter et al Science 246: 664, 1989.
Meijlink et al PNAS 82: 4987, 1985.
Shaw et al Cell 48: 659, 1986.

Mashall Science 270: 1751, 1995.

Coughlan New Scientist, 25 Nov. 1995 pp. 14–15.

Donahue et al JEM 176: 1125, 1992.

Orkin & Motulsky "Report & Recommendations of the Panel to Assess the NIH Investment in Research on Gene Therapy", Dec. 7, 1995.

*Primary Examiner*—Suzanne E. Ziska
*Attorney, Agent, or Firm*—Oblon, Spivak, McClelland, Maier & Neustadt, P.C.

[57] ABSTRACT

A peptide, Hel-N1, which can bind to a 3'-untranslated mRNA sequence (which encompasses the "instability sequence") that is uniquely present in the messenger RNAs that encode oncoproteins and lymphokines, and mediates the specific destruction of the messenger RNAs, is described. Full-length Hel-N1 is capable of suppressing cell growth and causing cellular differentiation. Hel-N1 possess three RNA recognition motifs. One of these forms an RNA-binding domain which, when transfected alone into cells, causes them to undergo rapid growth.

5 Claims, 10 Drawing Sheets

FIG. 1B

```
elav    ELEAIFAPFGAIIITSRILQNAGND----TQTKGVGFIRFDKREEA 303
Hel-NI  ELEQLFSQYGRIIITSRILVDQVT-----GISRGVGFIRFDKIREA 179
K3      DLESLFSPYGKIIITSRILCDNITDEHAAGLSKGVGFIRFDQRFEA 255

elav    TRAIIALNGTTPSSCTDPIVVKFSNTPGSTSKIIQPQLPAFLNPQ 348
Hel-NI  EEAIKGLNGQKPPGATEPITVKFANNPSQKTNQAILSQLYQSP-N 223
K3      DRAIKELNGTTPKNSTEPITVKFANNPSSNKNSMQPLAAYIAPQN 300

elav    LVRRIGGAMHTPVNKGLARFSPMAGDMLDVMLPNGLGAAAAAAII 393
Hel-NI  -R--R-YP-----GPLAQQAQRFRLDNLLNMAYGVKRFSPMTIDG 259
K3      TRGGRAFPANAAAGAAAAAAAAIHPNAGRYSSVISRYSPLTSDL 345

elav    LASGPGGAYP--------IFIYNLAPEIEEAALVQLFGPFGAVQS 430
Hel-NI  MTSLAGINIPGHPGTGVCIFVYNLAPDADESILVQMFGPFGAVTN 304
K3      IT-NGMIQGNTIASSGVCIFVYNLAPETEENVLVQLFGPFGAVQS 389

elav    VKIVKDPTTNQCKGYGFVSMTNYDEAAMAIRALNGYTMGNRVLQV 475
Hel-NI  VKVIRDFNTNKCKGFGFVTMTNYDEAAMAIRSLNGYRLGDRVLQV 349
K3      VKVIRDLQSNKCKGFGFVTMTNYEEAVLAIQSLNGYTLGNRVLQV 434

elav    SFKTNK-AK--                                   483
Hel-NI  SFKTNKTHKA-                                   359
K3      SFKTNK-NKQT                                   444
```

| SELECTED Hel-N1 RNA-BINDING SEQUENCES | FOUND IN mRNA INSTABILITY REGIONS |
|---|---|
| AUUUA | GM-CSF, α-β-γIFN, IL1-2-3, c-myc, c-myb |
| UUAUUUAUU | TNF, c-IFN, GM-CSF |
| AUUUUUA | βIFN, c-myb, c-fos, IgG1-IF, IL-2 |
| AUUUUA | βIFN, c-myc, IL-2, c-fos, c-myb |
| AUUUUC | βIFN |
| GUUUUUA | c-myc, c-fos |
| CUUUUUA | IFN, c-myc |
| AUUUUUUUC | c-myc |
| AUUUG | c-myb, c-myc |
| AUUUC | c-sis |
| CUUUUA | c-sis |
| CUUUA | IL-2 |

*FIG. 4*

```
                                        40                                      80                                      120
CCAATAGTAGTCATTTTAAATATATATTCTGAAATCTTTG CAAATTTTAACAGAAGAGTCGAAGCTCTGCGAGACCCAAT ATTTGCCAATAAGAATGGTTATGATAATTAGCACCATGGA
                                                                                                          M  V  M  I  I  S  T  M  E>

                                        160                                     200                                     240
GCCTCAGGTGTCAAATGGTCCGACATCCAATACAAGCAAT GGACCCTCCAGCAACAACAGAAACTGTCCTTCTCCCATGC AAACAGGGGCAACCACAGATGACAGCAAAACCAACCTCAT
 P  Q  V  S  N  G  P  T  S  N  T  S  N   G  P  S  S  N  N  R  N  C  P  S  P  M   Q  T  G  A  T  T  D  D  S  K  T  N  L  I>

                                        280                                     320                                     360
CGTCAACTATTTACCCCAGAATATGACCCAAGAAGAATTC AGGAGTCTCTTCGGGAGCATTGGTGAAATAGAATCCTGCA AACTTGTGAGAGACAAAATTACAGGACAGAGTTTAGGGTA
 V  N  Y  L  P  Q  N  M  T  Q  E  E  F   R  S  L  F  G  S  I  G  E  I  E  S  C   K  L  V  R  D  K  I  T  G  G  S  L  G  Y>

                                        400                                     440                                     480
TGGATTTGTTAACTATATTGATCCAAAGGATGCAGAGAAA GCCATCAACACTTTAAATGGACTCAGACTCCAGACCAAAA CCATAAAGGTCTCATATGCCCGTCCGAGCTCTGCCTCAAT
 G  F  V  N  Y  I  D  P  K  D  A  E  K   A  I  N  T  L  N  G  L  R  L  Q  T  K   T  I  K  V  S  Y  A  R  P  S  S  A  S  I>

                                        520                                     560                                     600
CAGGGATGCTAACCTCTATGTTAGCGGCCTTCCCAAAACC ATGACCCAGAAGGAACTGGAGCAACTTTTCTCGCAATACG GCCGTATCATCACCTCACGAATCCTGGTTGATCAAGTCAC
 R  D  A  N  L  Y  V  S  G  L  P  K  T   M  T  Q  K  B  L  B  Q  L  F  S  Q  Y   G  R  I  I  T  S  R  I  L  V  D  Q  V  T>
```

*FIG. 6A*

```
                                          880                                      920                                      960
GCTTAATATGGCCTATGGCGTAAAGAGACTGATGTCTGGA CCAGTCCCCCCTTGTGCTTGTTCCCCCAGGTTCTCCCCAA TTACCATTGATGGAATGACAAGCCTTGTGGGAATGAACAT
 L  N  M  A  Y  G  V  K  R  L  M  S  G   P  V  P  P  S  A  C  S  P  R  F  S  P   I  T  I  D  G  M  T  S  L  V  G  M  N  I>
                                         1000                                     1040                                     1080
CCCTGGTCACACAGGAACTGGGTGGTGCATCTTTGTCTAC AACCTGTCCCCCGATTCCGATGAGAGTGTCCTCTGGCAGC TCTTTGGCCCCTTTGGAGCAGTGAACAACGTAAAGGTGAT
 P  G  N  T  G  T  G  W  S  I  F  V  Y   N  L  S  P  D  S  D  E  S  V  L  W  Q   L  F  G  P  F  G  A  V  N  N  V  K  V  I>
                                         1120                                     1160                                     1200
TCGTGACTTCAACACCAACAAGTGCAAGGGATTCGGCTTT GTCACCATGACCAACTATGATGAGGCGGCCATGGCCATCG CCAGCCTCAACGGGTACCGCCTGGGAGACAGAGTGTTGCA
 R  D  F  N  T  N  K  C  K  G  P  G  F   V  T  M  T  N  Y  D  E  A  A  M  A  I   A  S  L  N  G  Y  R  L  G  D  R  V  L  Q>
                                         1240                                     1280                                     1320
AGTTTCCTTTAAAACCAACAAAGCCCACAAGTCCTGAATT TCCCATTCTTACTTACTAAAATATATATAGAAATATATAC GAACAAAACACACGCGCGCACACACACACATACACGAAAG
 V  S  F  K  T  N  K  A  N  K  S>
                                         1360                                     1400                                     1440
AGAGAGAAACAAACTTTTCAAGGCTTATATTCAACCATGG ACTTTATAAGCCAGTGTTGCCTAGTATTAAAACATTGGGT TATCCTGAGGTGTACCAGGAAAGGATTATAATGCTTAGAA

AAAAAAAAAGAAAAAAAAAAAACAAAAAA
```

FIG. 6B

METHODS AND COMPOSITIONS INVOLVED IN CELL GROWTH, NEOPLASIA AND IMMUNOREGULATION

This is a Division of application Ser. No. 07/881,075 filed on May 11, 1992, now U.S. Pat. No. 5,444,148.

BACKGROUND IF THE INVENTION

1. Field of the Invention:

This invention relates to proteins which contain amino acid sequences that bind to 3'-untranslated regions of mRNAs, particularly mRNA sequences containing "instability sequences" (Shaw et al, *Cell* (1986) 46:659–667).

2. Discussion of the Background

General features of primary sequence that characterize RNA- and DNA-binding proteins have begun to become apparent. The helix-turn-helix (Pabo et al, *Annu. Rev. Biochem.*, (1984) 53:293–321) and zinc-binding finger (Evans et al, *Cell* 1988) 52:1–3) arrangements have both been observed as structural features of sequence-specific DNA-binding proteins. In eukaryotes, the homeobox domain seems to represent a widespread primary sequence motif for specific DNA-binding (Levine et al, *Cell* (1988) 55:537–540; Robertson, *Nature* (1988) 336:522–524, and references therein), and the members of the steroid hormone receptor superfamily of DNA-binding proteins utilize a common motif which forms zinc-binding fingers (Evans, *Science* (1988) 240:889–895).

Early on RNA-binding proteins were less well studied than DNA-binding proteins; general features of RNA-binding proteins were not evident until the recognition of an amino acid octamer present in four proteins associated with mammalian nuclear RNAs (Adam et al, *Mol. Cell Biol.* (1986) 6: 2932–2943). The recognition of RNA by proteins has appeared to the inventors to be a key reaction in the regulation of expression of the genetic material of all cells.

One of the present inventors has studied RNA binding proteins of this group for many years and in 1983 isolated the first eukaryotic recombinant cDNA member of this family of proteins that encodes the human La RNA binding protein (Chambers et al, *Proc. Natl. Acad. Sci.* (USA) (1985) 82: 2115–2119; Chambers et al, *J. Biol. Chem.*(1988) 263: 18043–18051).

Subsequently, the observation by Dreyfuss and coworkers (Adam et al, *Mol. Cell. Biol.* (1986) 6:2932–2943; Swanson et al, *Mol. Cell. Biol.* (1987) 1:1731–1739) of an "RNP consensus" octamer in several eukaryotic proteins associated with RNA was an early indication that an amino acid sequence common among some RNA-binding proteins might exist.

Other publications by the Dreyfuss group (Dreyfuss et al, *TIBS* (1988) 13:86–91) and from many other laboratories (Amrein et al, *Cell* (1988) 55, 1025–1035; Bell et al, *Cell* (1988) 55, 1037–1046; Bugler et al, *J. Biol. Chem.* (1987) 262: 10922–1–925; Chambers et al (1988), ibid; Deutscher et al, *Proc. Natl. Acad. Sci* (USA) (1988) 85:9479–9483; Goralski et al, *Cell* (1989) 56, 1101–1108; Keene, J. D., *J. Autoimmunity* (1989) 2:329–337; Merrill et al, *J. Biol. Chem.* (1988) 263, 3307–3313; Sachs et al, *Mol. Cell. Biol.* (1986) 7, 3268–3276) noted the presence of related sequences surrounding the octamer and speculated that these regions might participate in RNA binding. It was not known at that time however whether these sequences might endow specific as opposed to nonspecific recognition of RNA or if discontinuous regions involving long-range interactions within these proteins might be required for RNA binding.

Some authors speculated that the octamer and its surrounding residues constituted an RNA binding domain and Dreyfuss and coauthors (ibid) chose an arbitrary size of 100 amino acids. Their theory was based upon the occurrence of similar sequences in a set of proteins that were all thought to be associated with RNA. Evidence for direct binding of such regions to specific RNA sequences was not available and no domains of proteins with binding activity were defined experimentally.

Included in this theory was the suggestion that the 70K U1 snRNP protein contained an RNA binding domain of 93 amino acids from positions 94 to 186. Other investigators (*Theissen* et al, *EMBO J.* (1986) 5:3209–3217) had speculated that a different region of the 70K U1 snRNP protein encompassing amino acid residues 241 to 437 as well as the same region speculated by Dreyfuss were either one or both involved in RNA binding. These speculations were based upon the relationship of the highly basic (positively charged) region at amino acids 241 to 437 of 70K protein to regions of other proteins (e.g., protamines and histones) known to bind nucleic acid. No experimental evidence was available to support these suggestions.

Although the 70K protein is one of ten proteins known to be associated with the U1 snRNP complex (Pettersson et al, *J. Biol. Chem.* (1984) 259:5907–5914), there was no evidence of specific RNA protein contact between the 70K protein and any RNA species until the discovery of a specific binding of the 70K protein to U1 RNA. Furthermore, of the other members of this group of proteins studied in our laboratory, as well as, in many other laboratories, none was shown to directly bind to a specific RNA sequence until one of the present inventors discovered the sequence-specific interaction between 70K U1 snRNP protein and U1 RNA.

The region of the protein involved in this specific binding involves a different amino acid sequence of 70K protein than that speculated by Theissen et al or by Dreyfuss et al. In fact, one of the sequences proposed by Theissen as being responsible for RNA binding actually interferes with the detection of specific binding activity.

In addition, the discovery of the precise RNA binding domain of the 70K protein includes additional important amino acid sequences not previously recognized by the theory of Dreyfuss et al, by the published work of other workers mentioned above or by some of the inventors themselves in their earlier studies of La (Chambers et al, ibid) and the 60 kD Ro (Deutscher et al, ibid) protein members of the group.

RNA binding proteins are now known to be involved in the control of a variety of cellular regulatory and developmental processes, such as RNA processing and compartmentalization, mRNA translation and viral gene expression. Some proteins that recognize and bind RNA can be classified into families based upon primary sequence homology, as well as higher order structure.

The family of RNA binding proteins containing an RNP consensus octamer and an 80 amino acid motif implicated in RNA recognition (RRM) has been the subject of intense investigation. Query et al, *Cell* (1989) 57:89–101; Kenan et al, *Trends Biochem. Sci.* (1991) 16:214–220. Based upon crystallographic and NMR spectroscopic studies of the U1 RNA binding domain of the U1 snRNP-A protein a model of the tertiary structure has been derived. The tertiary structural model together with RNA binding studies have led to the suggestion that the RNA binding surface resides on a monomeric unit with four anti-parallel β-strands which contains solvent exposed aromatic and basic residues.

Kenan et al (1991) supra. Additional biochemical data have demonstrated that a determinant of RNA binding specificity resides in a loop which connects two β-strands. Bentley et al, *Mol. Cell. Biol.* (1991) 11:1829–1839.

More than forty members of the RRM superfamily have been reported to date, the majority of which reside in all tissues and are ubiquitously conserved in phylogeny. Kenan et al (1991) supra. Tissue-specific members of the RRM family are less common, including X16 which is expressed in pre-B cells, Bj6 which is a puff-specific Drosophila protein and elav (embryonic lethal abnormal vision) which is neuronal-specific in Drosophila. For some RRM proteins the natural RNA ligands have been identified or surmised, but the RNA-binding sequences are not known in most cases.

The RNA ligands for the tissue-specific RRM proteins have not been reported and may prove difficult to determine because of their specialized roles in certain developmental processes. However, in order to understand their functions in cellular RNA metabolism and development, it will be essential to identify the RNA sequences to which they bind.

Oncogenes encode growth factors that affect the rate of cell proliferation by influencing cell cycle events such as mitosis, intracellular signaling pathways and gene expression. Some well known oncogenes are c-src, c-myc and c-fos. Lymphokines, which affect the growth properties of immunoregulatory cells, also function as growth factors similar to oncogene products. Although oncogene products (oncoproteins) are central components in the origin of the neoplastic state, they work through a variety of complex and largely unknown pathways. Consequently, methods to specifically control the functions of oncoproteins have not materialized.

The more recent discovery of suppressor oncogenes (anti-oncogenes) has held promise for being able to counter the effects of oncogenes. Some examples of anti-oncogenes include: retinoblastoma (Rb) and p53. It is hoped that these factors can be used to counter the effects of oncoproteins and thus, provide new treatments for cancer. For example, breast tumors show a consistent defect in the p53 gene, thus, preventing p53 from countering the oncogenes that cause uncontrolled proliferation of the breast tumors. Unfortunately, there are likely to be dozens of anti-oncogenes, each being specific to a given type of cancer.

Accordingly, there is a strongly felt need for the discovery of materials generally useful in the recognition, binding and/or expression of ribonucleic acids involved in the growth, neoplasia and immunoregulation. Such materials would have many uses, including regulation of cell proliferation in vitro and in vivo, regulation of immune cell expression, stimulation of cell growth, the production of transgenic animals and cell lines for pharmaceutical tests of cancer, immune function and neurological diseases, diagnostic reagents for the detection of autoantibodies associated with cancers, in vivo targeting systems, in diagnosing pathology specimens of neuronal origin, and/or as genetic or neurogenetic disease markers involving malformations of the central nervous system.

SUMMARY OF THE INVENTION

Accordingly, one object of this invention is to provide novel proteins which can bind to mRNAs which encode oncoproteins or lymphokines.

It is another object of this invention to provide novel proteins which can bind to 3'-untranslated regions of mRNAs, particularly mRNA "instability sequences", in eukaryotic cells.

It is another object of this invention to provide novel proteins, and their corresponding DNA and mRNA sequences, which can provide in cell cultures or in vivo modulation of the expression of oncogenes and/or lymphokine-encoding genes in eukaryotic cells.

It is another object of this invention to provide novel proteins, and their corresponding DNA and mRNA sequences, useful in the regulation of cell proliferation in cell cultures and in vivo.

It is another object of this invention to provide novel proteins, and their corresponding DNA and mRNA sequences, which can be used to take cells out of a proliferative state and into a state of differentiation.

It is another object of this invention to provide novel proteins, and their corresponding DNA and mRNA sequences, useful in the regulation of immune cell gene expression.

It is another object of this invention to provide novel proteins, and their corresponding DNA and mRNA sequences, useful for stimulating or suppressing mammalian cell growth.

It is another object of this invention to provide novel proteins, and their corresponding DNA and mRNA sequences, useful to produce transgenic animals and cell lines for pharmaceutical tests of cancer, immune function and/or neurological diseases.

It is another object of this invention to provide novel proteins, and their corresponding DNA and mRNA sequences, useful as diagnostic and/or therapeutic reagents for the detection or therapy of autoantibodies present in the body of a cancer patient.

It is another object of this invention to provide novel proteins, and their corresponding DNA and mRNA sequences, which can be used for the in vivo targeting of certain substances.

It is another object of this invention to provide novel proteins, and their corresponding DNA and mRNA sequences, useful for diagnosing pathology specimens of neuronal origin.

It is another object of this invention to provide novel proteins, and their corresponding DNA and mRNA sequences, useful as genetic or neurogenetic disease markers in the diagnosis and/or therapy of patients in need thereof.

The present invention which satisfies all of the above objects of the invention, and others as can be seen from the description of the invention given hereinbelow, relates to a novel protein, named Hel-N1 by the inventors, and related proteins, discovered by the inventors as being able to bind to 3'-untranslated mRNAs, including a sequence (the "instability sequence") that is uniquely present in the messenger RNAs that encode oncoproteins and lymphokines. The "instability sequence", discovered by Shaw et al (*Cell* (1986) 46:659–667), resides in the 3'-noncoding region of mRNAs which encode oncoproteins and lymphokines. The present invention also provides DNA and mRNA sequences corresponding to Hel-N1 and the related proteins.

BRIEF DESCRIPTION OF THE FIGURES

A more complete appreciation of the invention and many of its attendant advantages will be readily obtained as the same becomes better understood by reference to the following detailed description when considered in connection with the accompanying figures.

FIGS. 3 and 4 set forth RNA sequences selected to bind Hel-N1 using a random RNA selection procedure (Tsai et al *Nucl. Acids Res.,* (1991) 19:4931–4936). FIG. 3 sets forth thirty RNA sequences, 25 nucleotides in length, which were identified from clones generated by reverse transcription and PCR amplification of selected RNAs. Twenty seven of the sequences consistently contained short stretches of uridylate residues interspersed with other nucleotides (boxed region). Two of the U-rich sequences were obtained twice. The two selected sequences shown at the bottom of the figure (B-17 and B-5) lack the stretches of uridylates. FIG. 4 shows, among the sequences selected to bind Hel-N1 (FIG. 3), those that were found among the 3'-UTR instability sequences indicated by Shaw et al, *Cell* (1986) 46:659–667.

FIG. 6 sets forth the amino acid sequence of a paraneoplastic encephalomyelitis antigen, HuD, reported by Szabo et al, *Cell* (1991) 67:325–333.

DETAILED DESCRIPTION OF THE PREFERRED EMBODIMENTS

In this text, the following standard nomenclature is used.

TABLE 1

Amino acid symbols.

| Amino acid | Three-letter symbol | One-letter symbol |
|---|---|---|
| Alanine | Ala | A |
| Arginine | Arg | R |
| Asparagine | Asn | N |
| Aspartic acid | Asp | D |
| Asn + Asp | Asx | B |
| Cysteine | Cys | C |
| Glutamine | Gln | Q |
| Glutamic acid | Glu | E |
| Gln + Glu | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The inventors have been isolating and characterizing RNA binding proteins, and studying their RNA-binding specificities. More particularly, as described in greater detail in application Ser. Nos. 07/536,943 and 07/436,779, filed on Jun. 12, 1990 and Nov. 15, 1989, respectively, both of which are hereby incorporated by reference, in studying the RNA-binding properties of the U1 RNA-associated 70K protein to elucidate regions of RNA-protein interaction, one of the inventors of the present invention, together with others, identified a central amino acid sequence involved in the specificity of gene expression at the level of pre-messenger RNA splicing in cells. While several structural motifs of proteins important in sequence-specific DNA-binding had been identified (e.g., helix-turn-helix and zinc-binding fingers) and two primary sequence motifs recently have been implicated directly in DNA-binding (homeoboxes and sequences within the steroid receptor family which form zinc-binding fingers), the structure or primary sequences of RNA-binding domains were not known prior to the invention of application Serial Nos. 07/536,943 and 07/436,779.

Elav is known to be involved in the early development of the central nervous system (CNS). Homozygous mutations of this gene locus give rise to numerous structural defects and hypotrophy of the CNS leading to embryonic lethality. Its role in neuronal growth and differentiation of the Drosophila nervous system is also underscored by the temporal appearance of elav transcripts during the differentiation of neuroblasts into primitive neurons.

Figure 1A:
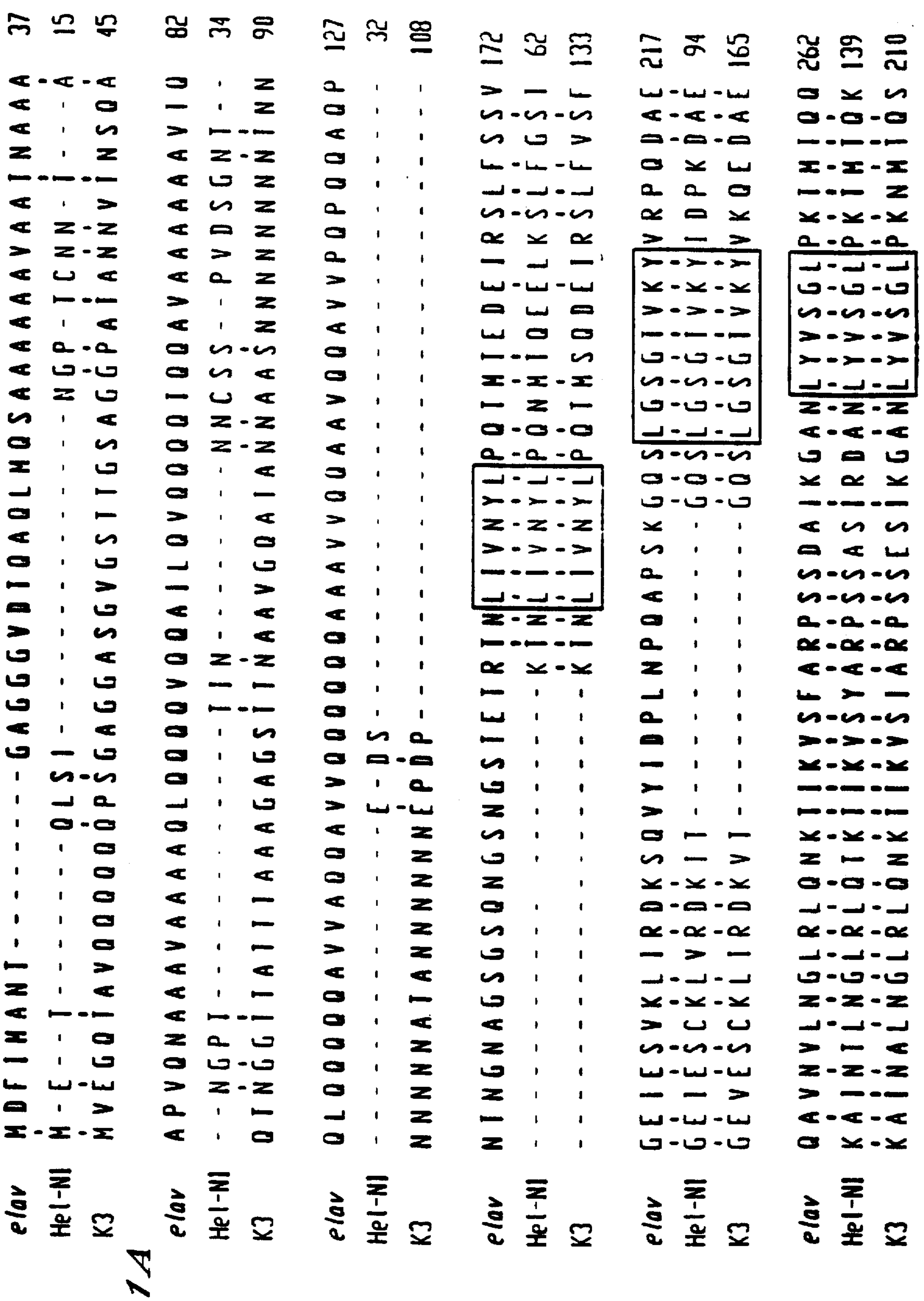
FIG. 1 provides an amino acid sequence comparison of two Drosophila neuron-specific proteins, elav and K3, with that of the human counterpart, Hel-N1. Open boxes represent the RNP2 consensus sequences of each RNA recognition motif, whereas, shaded boxes represent RNP1 consensus sequence. Vertical lines denote identical residues and hyphens denote gaps used to allow optimal alignment among the three sequences.

In probing for rat and human elav counterparts, the inventors relied on a novel approach of using degenerate primers designed to simulate the RNP-1 octamer sequence present in two of the three RRMs of Drosophila elav and thereby isolated cDNA encoding a novel neuron-specific protein, named Hel-N1 by them, from human brain by a combination of degenerate PCR probing and hybridization and found it to contain three RNA-recognition motifs (RRMs)*. FIG. 1 provides the complete amino acid sequence of Hel-N1.

*The term "recognition motif" is used herein to designate an amino acid relationship; the term "RNA binding domain" designates a peptide segment shown to possess binding activity.

Figure 5:
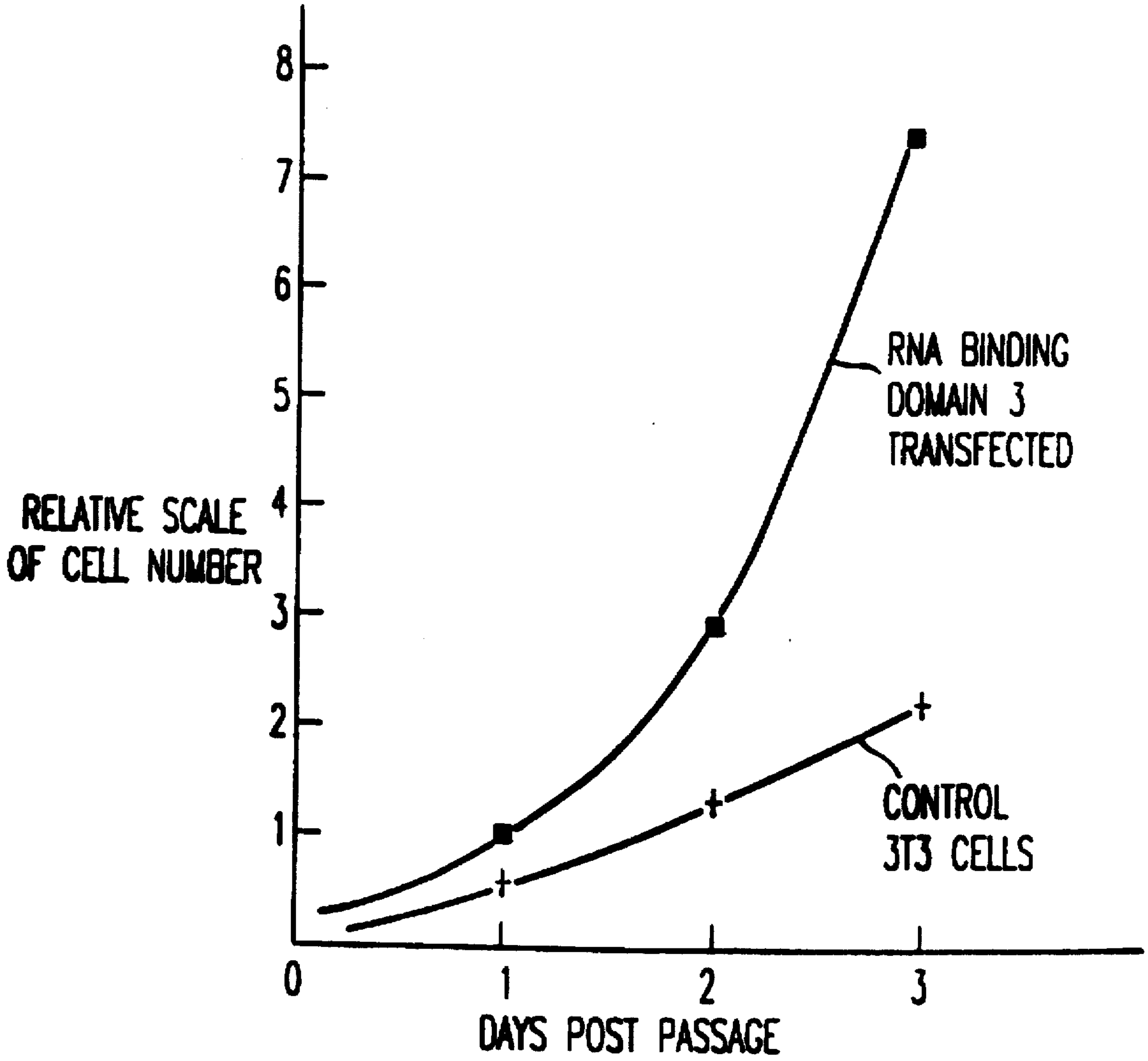
FIG. 5 illustrates a cellular growth curve obtained in accordance with the invention.

In in vitro studies they found that, in RNA binding, Hel-N1 prefers short stretches of uridylate residues and can bind the 3'-untranslated regions of c-myc, c-fos, and GM-CSF messenger RNAs, and that although Hel-N1 has three RRMs, only the third one (the most C-terminal binding domain situated between about amino acid positions 259 and 359) is responsible for mRNA 3'-untranslated region (which encompasses the instability sequence) binding activity. The inventors further discovered that full length Hel-N1, when transfected into a cell, caused cellular growth to cease. But, by contrast, and quite surprisingly, when only the third RNA binding domain was transfected into cells, the opposite result was obtained—the cells underwent rapid growth (as illustrated in FIG. 5).

Figure 7:
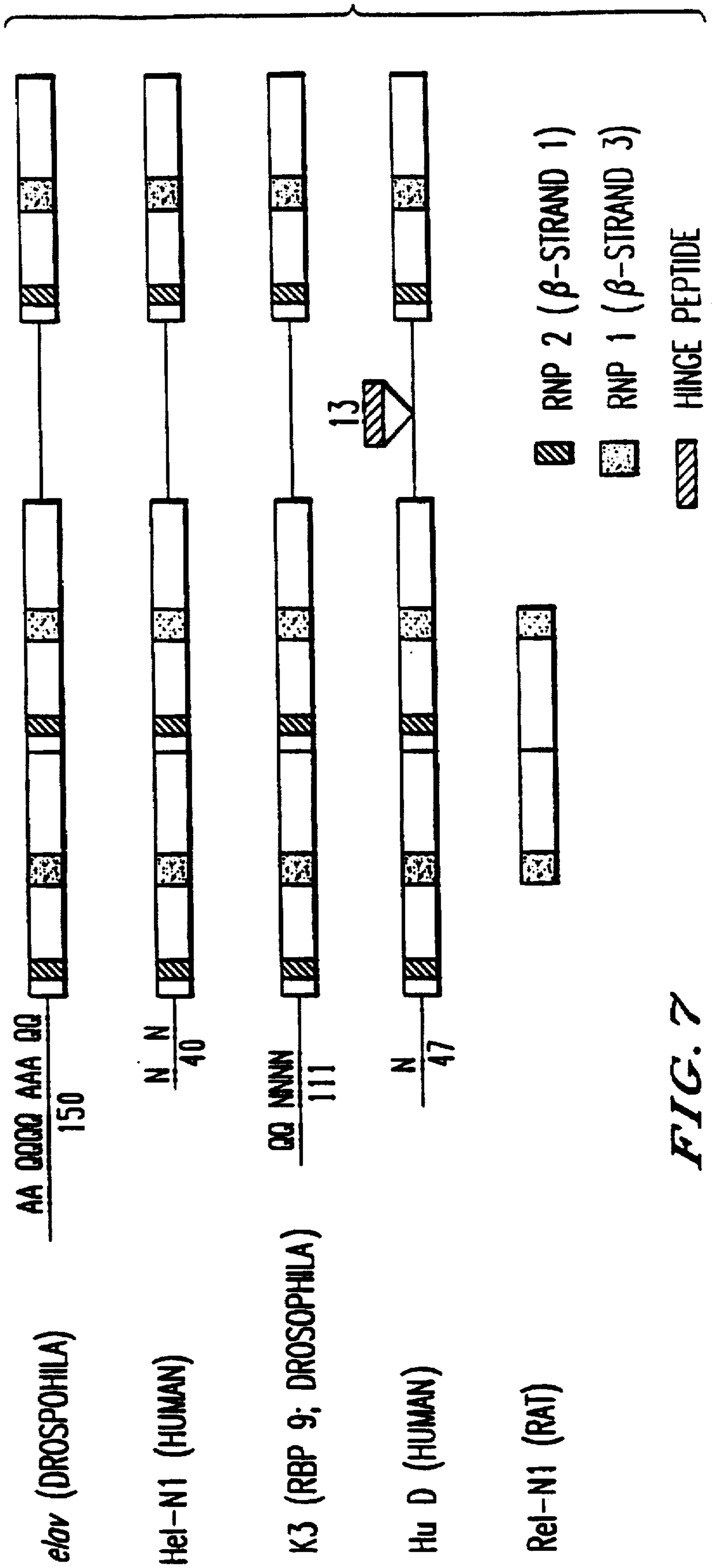
FIG. 7 is a comparative diagram of elav subfamily members' amino acid sequence.

It is not clear at this point whether transfection with the third RNA binding domain alone causes cellular transformation in the sense of an oncogene. RNA binding data obtained to date indicates that the single domain alone interferes with the ability of the full length Hel-N1 protein to bind in a multimeric fashion along the unstable oncoprotein or lymphokine mRNA. Thus, apparently the mRNA is rendered more stable and thus, more rapid proliferation results. In this sense, RBD3 may be a dominant negative suppressor of the instability function of Hel-N1. The inventors' data demonstrates that the Hel-N1 protein binds as a multimer along the mRNA, presumably enhancing its instability and/or regulating its translatability and/or deadenylating it (thus, less proliferation). This protein may be responsible for the growth cessation of neurons. Interestingly, recently Szabo et al (*Cell* (1991) 67:325–333) reported the isolation of a cDNA encoding another human protein, termed HuD, based upon its reactivity with antisera from patients with paraneoplastic encephalomyelitis. But Szabo et al do not describe any binding by HuD to mRNA 3'-untranslated sequences, or mRNA instability sequences. HuD is also homologous to elav in the RRMs, but differs from elav, K3 and Hel-N1 at its amino terminus and other places (see FIG. 7. Thus, it appears that four members of this subfamily have been identified and more are likely to be discovered.

Due to the high level of homology between them, the segments of elav found between amino acid positions about 393 and about 483, of K3 found between amino acid positions about 345 and about 444, and of HuD found between amino acid positions about 280 and about 380 can be used in accordance with the invention in lieu of the third domain of Hel-N1. (The amino acid sequences of elav and of K3 are set forth in FIG. 1, that for HuD is set forth in FIG. 6.)

The present invention thus relates to the Hel-N1 protein, to its third domain and related elav K3 and HuD segments, and to the exploitation of any of these proteins and their binding reaction to the 3'-untranslated regions containing the instability sequence of oncoprotein and lymphokine mRNAs (Shaw et al, 1986) as well as to different structural fusions that can be produced to target these mRNAs for up or down regulation.

The present proteins, namely either full length Hel-N1 or its third domain, can be used to obtain a binding reaction between two ligands in a manner analogous to that described in application Ser. Nos. 07/536,943 and 07/436,779, noted supra. For example, any number of other adducts (RNA or protein) can be attached to either of these ligands to create novel and useful ribonucleoproteins, or a ribonuclease can be attached to the RNA binding domain 3 using known techniques to directly target any of these mRNAs for destruction.

The proteins of the present invention can therefore be used as therapeutic reagents to provide for either growth suppression or growth stimulation. Full-length Hel-N1 can be used to cause growth suppression of cultured cells, presumably mediated through effects on the stability of messenger RNAs encoding growth factors. In accordance with the present invention, one can alter the growth properties of cells in which oncogenes and lymphokine genes are overexpressed. Thus, cancer cells, which may be targeted by any known standard means, including gene therapy, liposome-mediated delivery, retrovirus-mediated infection or direct infusion with Hel-N1 DNA, RNA or protein will consequently be retarded in their growth.

Likewise, immune cells regulated by lymphokines, such as interleukins, interferons and others can be growth suppressed using Hel-N1. In this embodiment, leukemic and lymphocytic cells targeted by delivery of Hel-N1 DNA, RNA or protein to the bone, thymus or bloodstream using known techniques become incapacitated. For example, immune B or T cells overproducing autoantibodies or other harmful antibodies can be targeted using antigens or antibodies imbedded in lyposomes or other known carriers which in turn, deliver Hel-N1 DNA, RNA or protein as a growth suppressor to destroy their ability to proliferate. The cells producing the harmful antibodies become thus incapacitated and immunosuppressive therapy can be enhanced in a specific manner.

In these regiments, Hel-N1 DNA, RNA or protein can be injected directly into cancer patients using known techniques to affect tumor growth. Likewise it can be injected into patients to suppress the proliferation of immune cells. Thus, with many variations on these themes, it can be seen that delivery of Hel-N1 DNA, RNA or protein which can block cell proliferation by suppression of growth factor messenger RNAs is highly advantageous.

As noted above, the inventors have found that the third RNA recognition motif of Hel-N1, found between amino acid positions 259 and about 349 of the Hel-N1 amino acid sequence provided in FIG. 1, constitutes the core of the oncoprotein and lymphokine mRNA binding domain. This approximately amino acid-long fragment is responsible for the specific instability sequence binding activity.

The inventors also made the startling discovery that expression of this domain, by itself, results in rapid proliferation of cells. This is a result opposite to that obtained by using full length Hel-N1. Expression of RNA binding domain 3 of Hel-N1 caused an eightfold increase in the growth of cultured cells after 3 days, as illustrated in FIG. 5. This is a striking alteration in a rate of proliferation. Thus, the RNA binding fragment of the growth suppression protein, Hel-N1, can itself be used to lead to the reverse effects, rapid cell growth.

Delivery of this fragment to tissue can be used to regenerate growth of cells in that tissue. One can use this embodiment to regenerate nervous tissue, heart tissue, skin and other tissues of limbs and organs. Likewise, RNA binding domain 3 can be delivered to tissues involved in wound healing and at other sites that are unable to be otherwise stimulated. Immune cells that produce autoantibodies and other factors needed for protection of the body can be growth stimulated using this invention.

Hel-N1 is an autoimmune protein in certain patients who show central nervous system manifestations of cancer called paraneoplastic cerebellar degeneration of (PCD), paraneoplastic encephalomyelitis (PE) or paraneoplastic sensory neuropathy (PSN). A therapeutic regiment could involve injection of Hel-N1 or peptides derived from Hel-N1 in order to block the immune effect or cellular immune recognition for properties in these diseases. Large amounts of pure Hel-N1 or its third domain are readily available using standard DNA cloning technologies or protein synthesis technologies. The purified protein can be used for immuno depletion of harmful autoantibodies or autoantibody—producing cells using methods of apheresis or dialysis.

The inventors also surprisingly discovered that full-length Hel-N1 can take cells out of a proliferative state and into a state of differentiation. Illustratively, whereas the third RNA binding domain of Hel-N1 was discovered to cause increased cell growth and the whole Hel-N1 protein discovered to cause cessation of cell growth, the inventors also observed that when certain neuroblastoma cells of (B104) were subjected to expression of whole Hel-N1 protein the cells developed an altered morphology. The cells became elongated like muscle cells and began to produce myotubules consisting of myosin and actin fibrils.

A cell derived from brain tissue was caused to enter an apparent myogenic pathway of differentiation by use of a protein of the present invention. This effect was due to the presence of a growth factor whose mRNA contained an instability sequence to which Hel-N1 was able to bind. In this case, the growth factor appears to be the Id protein which is known to suppress muscle differentiation. In the case of other similar growth factors, Hel-N1 may affect the differentiation of any cell which depends upon the continued expression of a growth factor encoded by an mRNA containing an instability sequence.

Thus, in another embodiment, Hel-N1 can be used in somatic or germline therapy to cause cells to undergo a desired pathway of differentiation. Hel-N1 has the further ability to control the balance between proliferation and differentiation that determines the developmental versus neoplastic consequences of gene expression.

The proteins of the present invention are also useful in therapeutic testing. An important need in the field of cancer research and immunology is for animal models which manifest altered growth properties or immune disregulation. Transgenic expression of polypeptides described in this application, using known techniques, can provide animals in which specific tissues or organs have been targeted to proliferate more rapidly or more slowly, thus allowing animal models of cancer or immune regulation to be produced. These animals are useful for testing the effect of chemotherapeutic drugs, radiation therapies, immune irregulatory agents, such as immunosuppressors and immunostimulators. Furthermore, Hel-N1 is itself an autoantigen to which patients with certain paraneoplastic diseases produce an autoantibody. The expression of Hel-N1 in transgenic tissues can allow production of an animal model for this autoimmune-type of cancer.

Proteins of the present invention are also useful in diagnostic applications. As a histological probe, Hel-N1 can be used to identify certain neuron types, such as granule cells or basket cells of the cerebellum. For example, in the pathology laboratory it is useful to stain cells with antibodies specific for Hel-N1 to determine the tissue origin of the specimen in question. Because Hel-N1 is present in certain neurons and not others, its presence in a tissue sample is an indicator of the type of tissue being examined.

Hel-N1 DNA constitutes a novel genetic marker for potential malformations of the central nervous system. For example, in the testing for genetic defects during prenatal examinations, many normal as well as abnormal markers are needed. For example, Hel-N1, in keeping with known oncogenes and antioncogenes, may be defective in patients suffering from natural cancers and leukemias. Full-length Hel-N1 DNA, RNA or protein may be used in the diagnosis and/or therapy of such individuals. Such therapy includes gene therapy, or targeted DNA, RNA or protein delivery. Hel-N1 is a useful, neuronal-specific probe. In testing for cystic fibrosis, Down's syndrome and similar genetic defects, one can get additional information on the status of CNS gene by monitoring Hel-N1 levels.

Thus in one embodiment, the present invention provides a polypeptide having the amino sequence of at least from the amino acid position 259 to 349 of Hel-N1 set forth in FIG. 1, and up to the whole amino acid sequence of Hel-N1. In another embodiment, the present invention provides a polypeptide which can be used to promote cell growth, where the polypeptide has the amino acid sequence of from amino acid position about 259 to about 349 of Hel-N1, or about position 393 to about position 483 of elav or about position 345 to about position 444 of K3, or about position 280 to about position 380 of HuD. In another embodiment, the present invention provides a polypeptide which can be used to suppress cell growth, and in particular expression of oncogenes and/or lymphokine encoding genes, by using a polypeptide having the whole amino acid sequence of Hel-N1.

In other embodiments, the present invention provides the corresponding DNA sequences and RNA sequences, optionally present in a liposome formulation, which may be either targeted or not targeted, or in a retroviral formulation, or in another formulation suitable for in vitro or in vivo delivery to cells or tissue. In other embodiments, these DNA and RNA sequences may be used in conjunction with gene therapy technology or to produce transgenic animals.

Another embodiment of the present invention relates to method for regenerating a mammalian tissue, including neuronal tissue, by administering to the tissue a polypeptide having the amino acid sequence of from about position 259 to about position 349 of Hel-N1 or the corresponding elav, K3 or HuD segments. The polypeptide may be administered to the tissue using any known means to deliver a polypeptide to a cell culture or in vivo to the cells of certain tissue, including gene therapy, liposome-mediated delivery, retrovirus-mediated infection, or direct infusion with the corresponding DNA, RNA or protein.

In another embodiment, the present invention is used to suppress the expression of an oncogene in a cell and/or of a lymphokine encoding gene in a cell, by causing the cell to express a polypeptide having about the whole amino acid sequence of Hel-N1. As with tissue regeneration, this may be achieved by using any standard means to cause the cell to express the desired polypeptide, including gene therapy, liposome-mediated delivery, retrovirus-mediated infection, or direct infusion with Hel-N1 DNA, RNA or protein. Particular oncogenes which may be targeted, include c-myc, c-fos or c-src, and others. Specific lymphokines which may be targeted in accordance with the present invention include GM-CSF, any interferon, or any interleukin, or others.

Hel-N1 and its associated DNAs and RNAs can also be used to produce transgenic animals and cell lines, using standard and known technologies, for pharmaceutical tests of cancer, immune functions and/or neurological diseases.

Having generally described this invention, a further understanding can be obtained by reference to certain specific examples which are provided herein for purposed of illustration only and are not intended to be limiting unless otherwise specified.

Hel-N1 and a rat cDNA, Rel-N1, appear to be homologous to Drosophila elav within the RNA recognition motifs; however, these proteins differ markedly in other regions. Analysis of mRNA expression in rat tissues demonstrated that Rel-N1, like elav, was specific to brain tissue. In situ hybridization localized Rel-N1 mRNA to neurons of the hippocampus and neocortex, but not to Purkinje cells, glial cells, or white matter.

The mRNA of the rat counterpart of elav was found to reside in a subset of neurons in the brain. It was not detected in glial cells or white matter and was found within the hippocampus and cerebral cortex of the rat. Using in vitro RNA binding methods, it was found that the human counterpart, Hel-N1 (Human elav-like Neuronal protein-1) could bind in vitro to the 3'-untranslated regions (3'-UTR) of certain mRNAs, including the mRNA "instability regions" of c-myc, c-fos and GM-CSF mRNAs.

These growth regulatory proteins are known to play important roles in cell proliferation, differentiation and immunoregulation. Thus, these observations show that Hel-N1, and perhaps other members of the elav sub-family, represent tissue-specific transacting factors involved in post-transcriptional mRNA metabolism.

Rat and human cDNA counterparts of the Drosophila neuronal protein, elav, were isolated using degenerate oligonucleotides, PCR, and library screening. RNAs capable of binding the human neuronal protein, Hel-N1, include 3'-UTRs of mRNAs encoding the oncoproteins, c-myc and c-fos and the lymphokine, GM-CSF. These RNA sequences encompass the "instability region" that is known to correlate with lability of these mRNAs (Meijlink et al, *Proc. Nat.*

*Acad. Sci.* (*USA*) (1985) 82:4987–4991; Shaw et al, *Cell* (1986) 46:659–667; Jones et al, *Mol. Cell Biol.*, (1987) 7:4513–4521).

RNA binding results were obtained using recombinant Hel-N1 followed by:(1) selection of uridylate stretches from a degenerate pool of RNAs, (2) immunoprecipitation of c-myc, c-fos and GM-CSF mRNAs using two types of Hel-N1-specific antibodies, and (3) crosslinking to c-myc and GM-CSF 3'-UTR with uv light. The 3-UTR of these mRNAs are U-rich, but also contain other identifiable features of primary sequence. For example, the pentameric sequence, AUUUA defined by Malter *Science* (1989) 246:664–666 and the octameric sequence, UUAUUUAU proposed by Caput et al, (1986), are common among the 3'-UTR of these mRNAs. These findings indicate that Hel-N1 and related proteins participate in the post-transcriptional regulation of unstable messenger RNAs.

Shaw et al *Cell* (1986) 46:659–667, demonstrated a role for the A/U-rich 3'-UTR of protooncogene and lymphokine mRNAs in the instability of the RNA. In addition, they demonstrated that instability could be conferred to otherwise stable mRNAs by placement of the instability region in the 3'-UTR.

However, it should be noted that other regions of certain mRNAs, including c-myc, c-fos, histone and transferin receptor, have also been implicated in destabilizing yhr mRNA (reviewed by Cleveland and Yen, 1989; Atwater et al, 1990). Verma and coworkers (Meijlink et al, 1985) demonstrated that removal of the 3'-UTR from c-fos mRNA resulted in increased levels of c-fos protein and cell transformation.

These studies show that regulatory events at the 3'-UTR are important for growth control. However, the A/U-rich 3'-UTR sequences span hundreds of nucleotides and the precise sequences involved in instability have not been identified. Recent work suggests that the AUUUA sequences are not required for instability, but that an upstream secondary structure in the 3'-UTR is more important. Thus, the role of the sequence elements within the 3'-UTR of these protooncogene and lymphokine mRNAs are not clearly defined at this time.

Proteins that interact with the 3'-UTR of oncoprotein and lymphokine mRNAs are poorly understood. Cross-linking with UV light and label transfer experiments by Vakalopoulou et al, *Mol. Cell. Biol.* (1991) 11:3355–3364, noted a 32 kD protein that binds this region. Malter, *Science* (1989) 246:664–666, observed a factor composed of three subunits, termed AUBF, in Jurkat cells that crosslinked to four repeats of the pentameric AUUUA sequence. More recently, Myer et al, *Proc. Nat. Acad. Sci.* (*USA*) (1992) found that small RNA transcripts from herpes simplex virus contain the AUUUA sequence and are capable of being UV cross-linked to the 32 kD protein from HeLa cell extracts. These findings suggest that there may be many proteins capable of recognizing sequences in the 3'-UTR. The binding specificity of Hel-N1 to the 3'-UTR of c-myc, c-fos, GM-CSF represents the only defined RNA-protein interaction in this region.

Using an in vitro RNA degradation assay Brewer (1991) identified and partially purified an activity termed, Auf, from human erythroleukemia cells that appears to be involved in instability of c-myc mRNA. Based upon a mobility shift assay, he postulated that proteins of 37 kD and a 40 kD present in these fractions were involved in binding to c-myc RNA. Although these factors were implicated in instability, they have not been characterized as to sequence or binding specificity. Hel-N1 represents an amino acid sequence containing an RNA-binding domain that can recognize and bind to 3'-UTR of mRNAs containing the instability sequence. It is possible that Hel-N1 represents a neuron-specific counterpart of one of several proteins shown to bind A/U-rich 3'-UTR sequences in UV crosslinking studies. Given that it contains three different RRMS, it appears that Hel-N1 functions as a structural component of an RNP which interacts in the 3'-UTR through one RNA binding domain and carries another small RNA to that site. Alternatively, the RNA binding domains could perform a structural role in RNA bridging interactions as proposed for the U1 snRNP-A protein (Lutz-Freyermuth et al, *Proc. Nat. Acad. Sci.* (*USA*) (1990) 87:6393–6397).

As an RNP or a bridging protein, Hel-N1 (or elav) may play a role in other post-transcriptional processes such as mRNA compartmentalization or translation. By this analogy, Hel-N1 may be involved in neuron-specific localization of mRNAs in the central nervous system.

Thus, members of the elav subfamily might recognize similar RNAs, but be functionally distinct based upon differences in their amino-terminal sequences. Expansion of the subfamily and determination of the tissue specificity and developmental regulation of each member will be required to address these possibilities.

Hel-N1, like HuD, was observed by the inventors to be reactive with an autoantibody present in the sera of patients with paraneoplastic disease, putting it in the category of other human autoantigens that are members of the RRM superfamily (Query et al, *Mol. Cell. Biol.* (1989), 9:4872–4881). The potential to bind to oncoprotein mRNAs adds an element of intrigue because these patients are a subset of those inflicted with small lung cell carcinoma in which levels of c-myc protein are elevated. However, the mechanism of initiation of the autoimmune response to these self antigens remains as elusive as that of the systemic snRNP autoantigens. In addition, there is no evidence that Hel-N1 or HuD play a role in the derivation of the paraneoplastic syndrome or of small cell carcinoma. Additional information concerning the influence of Hel-N1 and related proteins on the production of cellular growth factors will be required to argue for such a link.

cDNAs encoding a variety of putative RNA-binding proteins were isolated by probing with degenerate oligonucleotides derived from conserved portions of the RRM. For members of the RRM family that contain multiple RRMs, oligonucleotides derived from the sequence of the RNP1 octamers were used.

Primers representing sense and antisense strands of the RNP 1 of RRM 1 and the RNP 1 of RRM 2 of elav DNA (Robinow et al, *Science* (1986) 242:1570–1572) were used to probe mRNA from rat pup brain following reverse transcription with random primers. A PCR product was isolated and found to contain an ORF with an amino acid sequence termed, Rel-N1, which was, in turn, used to screen a human fetal brain library under high stringency conditions. A 2.2 kb DNA insert containing an open reading frame (ORF) of 359 amino acids was obtained. In vitro transcription and translation of the human cDNA produced a protein, termed Hel-N1, of the predicted size. Hel-N1 and Rel-N1 were identical in amino acid sequence and greater than 92% homologous in nucleic acid sequence.

Figure 2A:
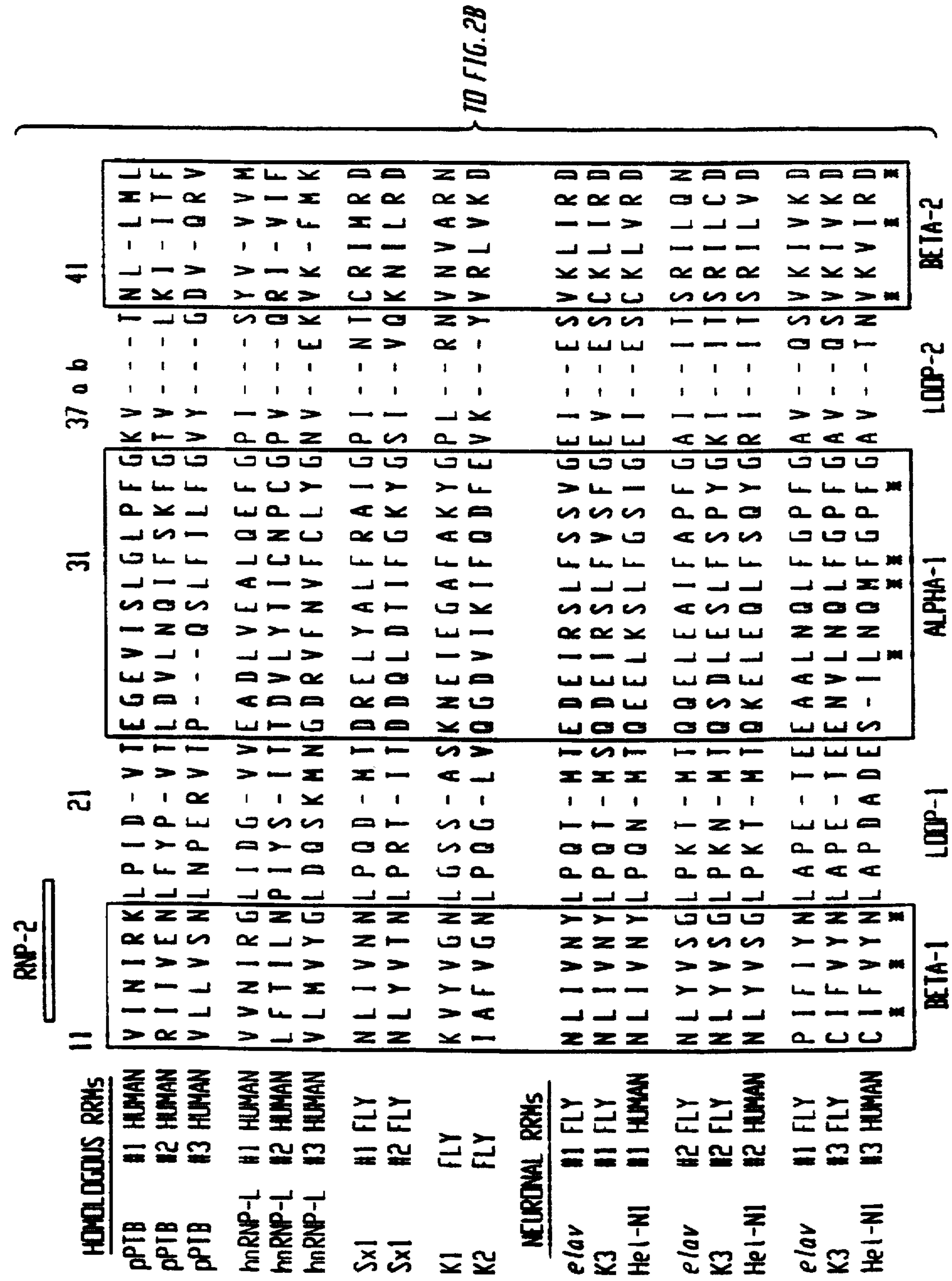
FIG. 2 provides a comparison of the three RRMs of elav, K3 and Hel-N1 with those of polypyrimidine tract binding protein (PPTB) (Garcia-Blanco et al, *Proc. Nat. Acad. Sci. USA* (1990) 87:3082–3086, hnRNP-L (Pinol-Roma et al, *J. Cell. Biol.* (1989) 109:2575–2587, Drosophila sex lethal (Sxl) and two other Drosophila proteins K1 and K2 as depicted by Kenan et al, (1991). Asterisks indicate key residues critical to the correct folding of the RNA binding domain.
Figure 2B:
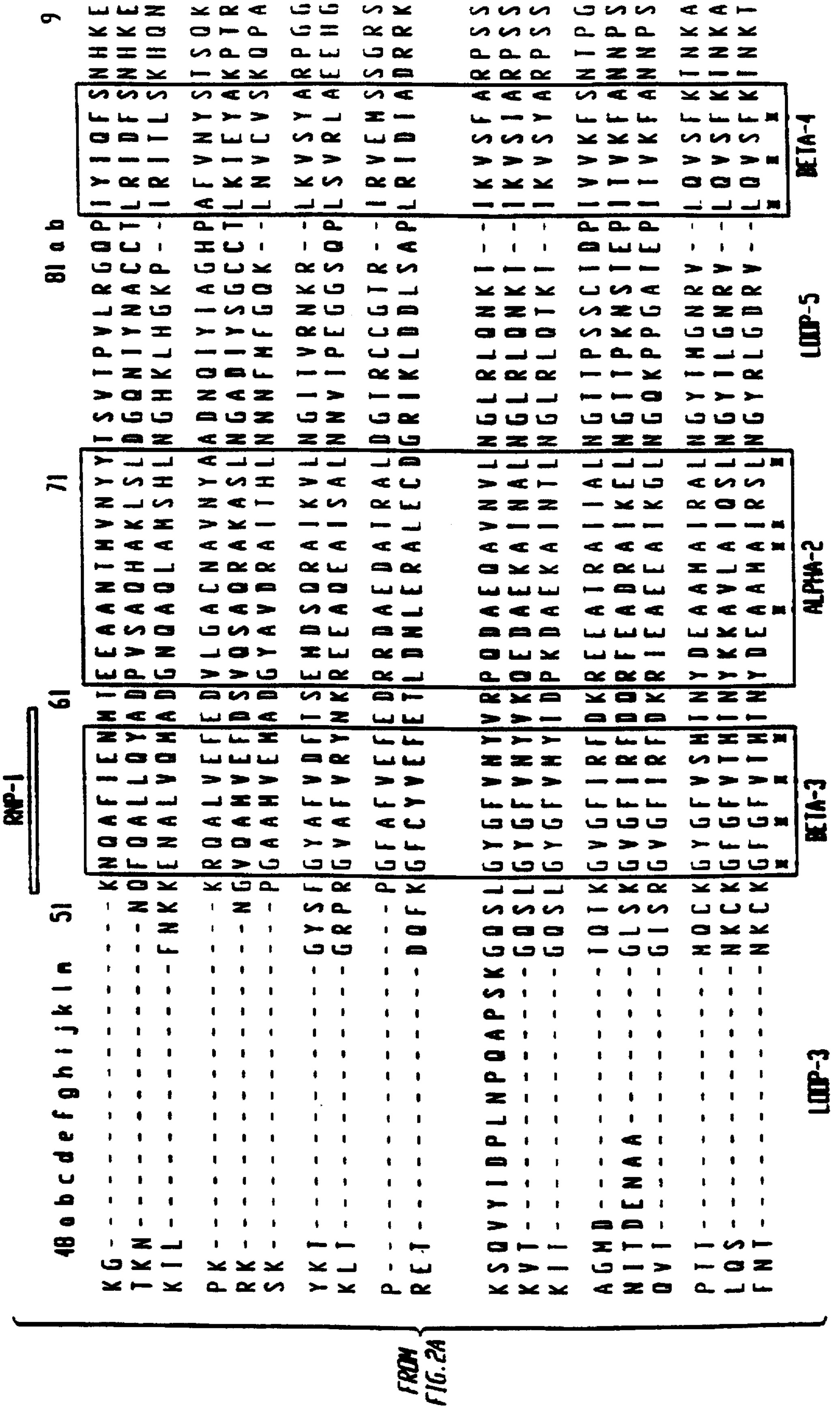
Figure 3:
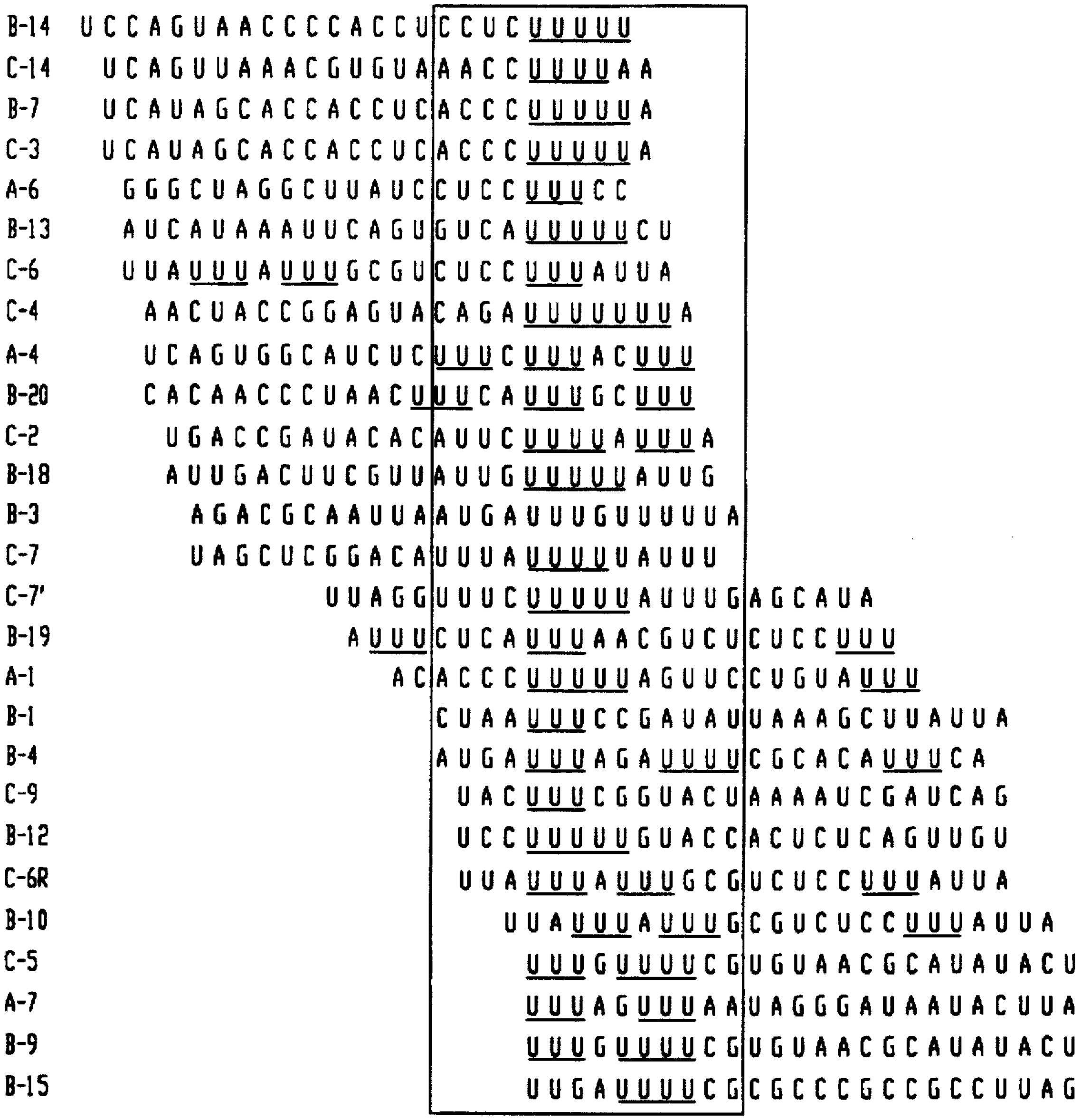

As shown in FIGS. 1 and 2, Hel-N1 contains three RNA binding domains as evidenced by RRMs 1, 2 and 3, which matched the structural criteria of Kenan et al (1991), supra, and each contained an RNP1 octamer (boxed and shaded) and an RNP2 hexamer (boxed) sequence. Sequence comparison of elav and a related Drosophila protein, K3, with Hel-N1, revealed strong similarities in the RRMs (FIGS. 1 and 2). On the other hand, Hel-N1 was only 76% the length of elav because the region amino terminal to the first RRM of the proteins demonstrated striking sequence differences (FIG. 1).

The amino terminus of Hel-N1 lacks the homopolymeric stretches of alanine, asparagine and glutamine seen in the amino termini of elav and K3, leaving it considerably shorter in length. This divergence is of unclear significance, especially in light of rescue studies done in Drosophila bearing the lethal mutation elavE5. These studies demonstrated that deletion of a 40 amino acid portion in the amino terminal does not prevent rescue from lethality. Thus, elav, Hel-N1 and K3 represent members of a subfamily of the RRM superfamily of RNA-associated proteins (Kenan et al, (1991), supra. This shows the existence of an elav-like subfamily of RNA binding proteins and, except for authentic elav, they can be designated by species as human (H) or rat (R) and tissue as neuronal (N) of origin.

Kenan et al, *Trends. Biochem. Sci.* (1991) 16:214–220, have proposed that pPTB and hnRNP-L represent a distinct subset of the RRM superfamily of RNA binding proteins in that they lack the characteristic RNP 1 and RNP 2 sequences. Also evident in FIG. 2 are the sequence differences in loop 3 that connects β-strand 2 to β-stand 3 (RNP 1). Loop 3 has been described as highly variable among RRM family members (Bentley et al, *Mol. Cell. Biol.* (1991) 11:1829–1839. In the case of the U1 snRNP-A protein, sequences residing in loop 3 were shown to affect the specificity of RNA recognition (Bentley et al, 1991; reviewed in Kenan et al, 1991); thus, representing one determinant of specificity. It is apparent that Hel-N1 differs from elav most strikingly in RRM 1, while RRMs 2 and 3 are highly similar (FIG. 2). This may indicate that the potential RNA-binding domains at RRM 1 of elav and Hel-N1 recognize very different RNA ligands.

Rel-N1 is neuron-specific

RNAs extracted from various rat tissues were analyzed by ribonuclease protection assays using Rel-N1 as probe. Protected bands were found only in RNA from rat brain; however, longer exposures revealed a small amount of RNA detectable in rat testes. To identify the specific neuroanatomic loci expressing Rel-N1 mRNA, 4% paraformaldehyde-fixed rat brain sections were hybridized with [35S]-labeled antisense RNA derived from the PCR fragment of Rel-N1 using the method of Fremeau et al, *EMBO J* (1990) 9:3533–3538.

Data revealed that Rel-N1 mRNA was heterogeneously distributed in adult rat brain. Prominent hybridization signals were observed throughout all layers of the cerebral cortex and within the hippocampus. High levels of expression were observed in the CA3–CA4 fields of Ammon's Horn. In contrast, only low levels of expression were observed in the CA1 field of Ammon's horn and the granule calls of the dentate gyrus. Prominent hybridization signals were also observed throughout the thalamus and brainstem. Particularly intense hybridization signals were observed in the parafascicular and midline thalamic nuclei. In the cerebellum, only a small percentage of labeled cells were observed in the granule cell layer while only background labeling was observed over the molecular layer, the Purkinje cell layer, and the white reafter tracts. Grains were not observed over the choroid plexus, ependymal cells of the cerebral ventricles, and control sections hybridized with a sense-strand probe.

In sum, these data indicate that Rel-N1 mRNA is expressed most highly in the hippocampus and cerebral cortex, as well as in certain neurons in the granule cell layer of the cerebellum, but not in Purkinje cells of the cerebellum.

Our initial approach, given that the RNA binding ligands are not known for any of the four known elav sub-family members, was to use several standard RNA binding assays (Lerner et al, *Proc. Nat. Acad. Sci.* (*USA*), (1979) 76: 5495–5499) using total 32P labeled RNA isolated from HeLa, glioblastoma and neuroblastoma cells. In addition, in vitro RNA binding procedures which have been used effectively for other members of the RRM family of proteins (Query et al, *Cell* (1989) 57:89–101; Lutz-Freyermuth et al, *Proc. Nat. Acad. Sci.* (*USA*), (1990) 87:6393–6397; Bentley et al, 1991) did not reveal a cognate RNA species for Hel-N1.

As an alternative approach, we used a random RNA selection procedure to define the RNA ligand site for Hel-N1. A synthetic oligodeoxynucleotide containing a stretch of 25 degenerate nucleotides was used to create a large heterogeneous pool of RNA sequences for selection of binding ligands (Tsai et al, *Nucl. Acids Res.* (1991) 19:4931–4936). Binding of the degenerate RNA pool to recombinant Hel-N1, followed by immunoprecipitation of the complex using the epitope tag, g10, was carried out as described previously (Lutz-Freyermuth et al, 1990; Bentley et al, 1991).

After three complete cycles of binding and selection, 30 independent clones, representing individual coimmunoprecipitated RNA species were evaluated by sequence analysis. The sequences of the bound RNAs showed a preponderance of uridylate residues in short stretches interrupted by other nucleotides. However, two of the 30 sequences (B-17 and B-5) did not contain this U-rich pattern. These variants were rare in the population and thus, may represent ligands of lower binding affinity. Alternatively, because Hel-N1 contains three potential RNA binding domains, these other sequences may represent ligands which were bound by one of the domains not involved in recognition of the U-rich regions. This possibility is compatible with the proposal that Hel-N1 may exist as an RNP that bridges between two or more RNAs via its multiple RRMs as proposed for the U1 snRNP-A protein (Lutz-Freyermuth et al, 1990).

This random RNA selection procedure has proved useful in our laboratory with other members of the RRM family of proteins to derive RNA ligand consensus sequences (Tsai et al, 1991), but in no other case has a U-rich sequence been selected. In the experiments using Hel-N1, RNA sequences with a Urich character were derived using the selection procedure, but a single consensus sequence was not evident.

The sequences selected from the in vitro RNA selection protocol were suggestive of biologically relevant sites known to exist in mammalian RNAs such as 3' UTRs in labile RNAs, the polypyrimidine tract near 3' splice junctions, sequence 5' of the polyadenylation signal, and in mitochondrial telomeres. The most striking feature was that short uridylate stretches flanked by either A, G or C could be located within the 3' UTRs listed by Shaw et al, *Cell* (1986) 46:659–667 in their study of the instability sequences of proto-oncogene and lymphokine messenger RNAs. Thus, we conducted a series of direct RNA binding experiments to examine this possibility.

DNA constructs encoding portions of the 3' UTR of c-myc, GM-CSF, and c-fos mRNAs were used to synthesize radiolabeled transcripts for binding to recombinant Hel-N1 protein using our standard methods (Bentley et al, 1991). We utilized $^{32}$p labeled transcripts corresponding to the 3' UTR sequences, as well as to a variety of unrelated RNAs. As with the RNA selection procedure used above, Hel-N1 was fused to the g10 epitope for precipitation. c-fos, GM-CSF and c-myc transcripts were precipitable, while other transcripts were not precipitable.

The specificity of Hel-N1 binding to 3'-UTR of c-myc, GM-CSF, and c-fos 3' UTR was substantiated by the use of many control RNAs including total HeLa cell RNA, transcripts of various small RNAs, precursor mRNAs, various vector RNA transcripts and other RNAs. In addition, RNA binding was always in the presence of carrier transfer RNA and poly A (Query et al, 1989; Bentley et al, 1991).

Control transcripts for RNA binding specificity also included hY3 antisense RNA that contained a single AUUUA pentamer. This sequence has been suggested to represent the most conserved element present in the 3' UTR of the unstable protooncogene and lymphokine RNAs (Shaw et al, *Cell* (1986) 46: 659–667; Caput et al, (1986); Malter, *Science* (1989) 246: 664–666. Vakalopoulou et al, *Mol. Cell. Biol.* (1990) 11:3355–3364, showed previously that the specificity for binding of these 3' UTRs to a 32 Kd protein present in Hela nuclear cell extracts resided in multiple copies of an AUUUA motif contained within a uridylate-rich region.

It should be noted that the hY3 RNA did not contain a uridylate-rich region surrounding the AUUUA. N-myc was also used as a control transcript because it contained a stretch of thirteen uridylates, but no AUUUA pentamer. None of these various control RNAs were significantly immunoprecipitated indicating that binding to Hel-N1 did not occur.

Among the control transcripts, we employed precursor mRNA-in-pieces (PIP vectors) which encode uridylate-rich stretches of RNA that are active in in vitro splicing and can be cross-linked with uv light to pPTB (Garcia-Blanco et al, 1990), supra. PIP transcripts also failed to bind Hel-N1. Several other RNA transcripts failed to bind Hel-N1 including coding regions of N-myc mRNA, U1 RNA, a transcript encoding neomycin resistance, noncoding regions of U1 snRNP-70K mRNA, and coding regions of the dopamine 1 receptor.

In these studies, RNAs in the supernatants of the binding reactions were analyzed for the presence of intact non-bound RNA to rule out degradation. Although Hel-N1 binding to other untested U-rich sequences remains a possibility, its preference for the instability sequences at the 3' UTR of c-myc, GM-CSF, and c-fos mRNAs was compelling.

As an alternative confirmation of the RNA-binding specificity of Hel-N1 with the 3'-UTRs of these rapidly degraded mRNAs, label transfer experiments involving uv crosslinking with 32P labeled RNA were performed using standard procedures. HeLa cell nuclear extract and recombinant Hel-N1 in an *E. coli* extract were incubated with 32P labeled c-myc or GM-CSF mRNAs and exposed to UV light to mediate covalent cross-linking between the RNA and associated proteins. After cross-linking, excess RNA was digested with RNase A and analyzed on an SDS-acrylamide gel.

The label transfer to Hel-N1 revealed two predominant bands of 70 kD and 28 kD; similar results were obtained with GM-CSF (data not shown). The higher molecular weight band was found to be an artifact of IPTG induction, since control *E. coli* extracts lacking Hel-N1 also showed the 70 kD cross-linked band. The 28 Kd band (termed Hel-N1') was 10 Kd smaller than the expected size of Hel-N1. While it is possible that the bound RNA or the cross-linking protocol caused Hel-N1 to migrate aberrantly, we observed that the 28 Kd band contained Hel-N1 epitopes (see below).

Direct label transfer experiments using HeLa cell extracts and radiolabeled c-myc mRNA demonstrated the ability to uv crosslink several proteins similar to that reported by Vakaloupoulu et al (1991). To determine whether Hel-N1 can compete with cross-linked proteins in the HeLa cell nuclear extract for binding to c-myc, increasing amounts of Hel-N1 were added prior to UV exposure. Neither the 32 kD protein identified by Valakpoulou et al (1991) nor hnRNP C protein (45 kD) diminished significantly upon addition of Hel-N1.

In addition, the 28 kD Hel-N1 band (Hel-N1') appeared during the crosslink competition.

These results indicate that Hel-N1, the 32 kD protein, and hnRNP-C protein can bind simultaneously to the 3'-UTR of c-myc MRNA. On the other hand, a band of 65 kD was competed by Hel-N1, while *E. coli* extracts lacking Hel-N1 had no effect. The identity of the competed 65 kD protein remains unknown. These data suggest that while the HeLa 32 Kd protein and hnRNP C may share similar RNA binding characteristics with Hel-N1, their binding sites as defined by uv crosslinking are not identical.

Recent studies into several paraneoplastic neurologic disorders including paraneoplastic sensory neuropathy (PSN), paraneoplastic cerebellar degeneration (PCD), and paraneoplastic encephalomyelitis (PEM) have reported the identification of several antigens recognized by the sera of patients with these disorders (Dropcho et al, *Proc. Nat. Acad. Sci. (USA)* (1987) 84:4552–4556; Anderson et al, *Neurology* (1988) 38:1018–1026; Dalmau et al, *Ann. Neurol.* (1990) 27: 544–557; Szabo et al, *Cell* (1991) 67:325–333).

One such antigen, HuD, displays strong similarity to recombinant Hel-N1, but possesses important differences. Both HuD and Hel-N1 contain three RRMs which share approximately 70% overall homology. The major differences exist in the amino termini and in a stretch of thirteen amino acids between the second and third RRMs.

Using anti-HuD sera, we demonstrated cross reactivity with Hel-N1 by Western blotting. When used in the RNA binding protocol in place of the gl 0 serum, an anti-Hu serum was found to immunoprecipitate c-myc transcripts that bound to Hel-N1 in vitro. Control RNAs did not bind Hel-N1. Furthermore, four normal human sera lacked the ability to immunoprecipitate these mRNPs. These experiments demonstrate that the complex formed between HuD antibodies and Hel-N1 does not interfere with the ability of the protein to recognize its RNA ligand.

To confirm the HuD RNA binding assay, the label transfer experiments using cmyc 3'-UTR and g 10-Hel-N1 as described above were followed by immunoprecipitation of the 28 Kd Hel-N1' band with HuD sera. Normal human sera were always negative. In addition, the 70 Kd *E. coli* band was not immunoprecipitated by any of these sera, as expected of the nonspecific *E. coli* protein. These data show that HuD sera can also immunoprecipitate a preformed complex of RNA bound to Hel-N1. Thus, Hel-N1, and presumably HuD, appear to possess autoantigenic epitopes that are distinct from the RNA-binding domain(s) that recognize the uridylates.

It is interesting to note that the 28 Kd band (Hel-N1') was immunoprecipitated with the HuD sera, but not with the g10 serum or normal sera. Thus, it was assumed that the amino terminus was lost by cleavage. Estimation of the resultant size of Hel-N1' suggests that cleavage occurred at a site C-terminal to the first RRM, leaving a fragment containing RRMs 2 and 3. The source of this unexpected cleavage event is currently under investigation. These results suggest that the interaction between c-myc mRNA and Hel-N1 is specific to the second or third RRM; one of which may constitute the RNA binding domain.

EXPERIMENTAL PROCEDURES

Cloning Rel-N1 and Hel-N1 by PCR and hybridization

Degenerate PCR primers were synthesized based on the first seven amino acids of the RNP1 consensus sequence in the first (sense) and second (antisense) RRMs of elav. Inosine residues were placed in positions degenerate for all 4 nucleotides and Eco R1 restriction sites were placed at the 5' end of each oligonucleotide. cDNA was prepared by reverse transcribing total cytoplasmic RNA from a Sprague-Dawley rat pup brain according to the manufacturer's specifications (Cetus®):6mg total RNA, 1 mM dNTPs, 100 picomoles of random hexamers (Pharmacia®), GeneAmp buffer, 20 U RNASIN (Promega®), 200U BRL reverse transcriptase. 40 cycles of PCR amplification were carried out using an annealing temperature of 37 and an extension temperature of 55 C. (cycles 1–4) and 72 (cycles 540). A PCR product of 281 bp was purified on a 1% agarose gel using Geneclean® (Bio 101) and subcloned into a TA vector (in Vitrogen®). The clone Rel-N1, was sequenced and found to have a high degree of homology with elav, including a 100% homologous RNP2 consensus sequence within the second RRM.

A random primed cDNA probe was generated using Rel-N1 and used to screen a λZAPII human fetal brain library (Stratagene®). Seven positive plaques were isolated from an initial population of 500,000 phage screened using the following hybridization conditions:50% formamide, 6× SSC, 0.1% SDS and 0.01% Blotto. Filters were hybridized for 18 hours at 42 C. and then washed two times at room temperature (10 minutes each) in 2× SSC/0.1% SDS followed by a final wash at 65 C. in 0.2× SSC/0.1% SDS for 45 minutes. The Bluescript® plasmids of the positive phage were then isolated according to the manufacturer's specifications (Stratagene®).

Sequencing Hel-N1 cDNA

EcoR1 inserts within the Bluescript® plasmids were sequenced by exonuclease digestion and primer extension using the dideoxynucleotide chain termination with a modified T7 DNA polymerase from the Sequenase system (USB). Oligonucleotides were synthesized on an Applied Biosystems® 391 DNA synthesizer.

Expression of Hel-N1 in *E. coli*

An inducible T7 RNA polymerase expression system (Studier-ref 20 in Donald's paper) was used for production of Hel-N1 protein. By using PCR mutagenesis, a conservative point mutation was introduced into the carboxy portion of the ORF to delete an NcoI site, such that the only NcoI site remaining was at the translation-initiation methionine. An NcoI—EcoR1 insert from this construct was then subcloned in frame into pET-3c containing the T7 12-amino acid (g10) sequence at the 5' cloning site. After transfection of this construct into BL21(DE3)pLysS, the bacteria were induced with IPTG. The cells were washed twice in SM buffer and then resuspended in a small volume of *E. coli* lysis buffer (1 × TBS, 10 mM EDTA, 0.05% Tween, 3mM DTT and PMSF). Lysis was completed by freeze-thawing the cells. The extract was centrifuged at 10,000×g to remove insoluble debris. The amount of induction was evaluated by sodium dodecylsulfatepolyacrylamide gel electrophoresis and Western blotting as well as Coomassie staining.

In situ Hybridization

In situ hybridization was conducted on 4% paraformaldehyde-postfixed adult rat brain sections as previously described (Fremeau et al, *EMBO J* (1990) 9:3533–3538). Briefly, adult Sprague-Dawley rats were anesthetized with 300 mg of sodium pentobarbital, and killed by decapitation. Brains were removed and frozen on an aluminum block cooled with liquid nitrogen. Frozen sections (10 u) were prepared in a cryostat, mounted onto room temperature slides (Onasco Biotech®; Houston, Tex.) and stored at -70° C. until processed for in situ hybridization.

Tissue sections were thawed and fixed for 10 min in 4% paraformaldehyde in phosphate-buffered saline at 4° C. The sections were then rinsed in 2× SSC, covered with a minimal volume of 2× SSC, and illuminated with a germicidal UV-lamp (30W, wide spectrum UV light) for 5 min at a distance of 30 cm. The sections were then rinsed in 2× SSC, and covered with prehybridization buffer (50% formamide, 0.6M NaCl, 10mM Tris-HCl (pH 7.5), 0.02% Ficoll, 0.02% polyvinyl pyrollidine, 0.1% bovine serum albumin, 1mM EDTA (pH 8.0), 50 ug/ml salmon sperm DNA, 500 ug/ml yeast total RNA, 50 ug/ml yeast tRNA and stored at 50° C. for 1 hr.

Prehybridization buffer was removed, and the slides were covered with hybridization buffer (50% formamide, 0.6M NaCl, 10mM Tris-HCl (pH 7.5) 0.02% Ficoll, 0.02% polyvinyl pyrollidone, 0.1% bovine serum albumin, 1 mM EDTA (pH 8.0), 10 ug/ml salmon sperm DNA, 50 ug/ml yeast total RNA, 50 ug/ml yeast tRNA, 10mM dithiothreitol, 10% dextran sulphate containing 35S-labeled probes (2.5–5.0× $10^6$ cpm/ml; heat-denatured for 15 min at 65° C.).

Hybridization was performed for 16–18 hrs at 50° C. Following hybridization, the sections were washed for 60 min in 2× SSC at 50° C. and then treated with RNase A (50 ug/ml) for 60 min at 37° C. The sections were then washed in 2× SSC for 60 min at 50° C. followed by a final high stringency wash in 0.1× SSC, 14 mM b-mercaptoethanol, 0.15% sodium pyrophosphate for 3 hr at 50° C., the heat was then turned off and the slides were allowed to gradually cool to room temperature overnight. The hybridized sections were dehydrated through graded ethanols containing 0.3M ammonium acetate, vacuum dried, and dipped in Kodak® NTB2 emulsion diluted 1:1 with $H_2O$. After 4–6 week exposure times, the slides were developed as previously described (Fremeau et al, 1990) and photographed under dark-field illumination with kodachrome 160 tungsten slide film (Kodak®).

RNA Probes

Rel-N1 cDNA was excised from the TA vector and subcloned into pGEM-3Zf(+) and linearized. $^{35}S$ (for in situ hybridization) or 32P (for RNAse protection assay) labeled single stranded antisense RNA probes were synthesized using T7 RNA polymerase in the presence of [35S]UTP (New England Nuclear®) or [32P]UTP (ICN). Sense RNA probe, made in a similar way, was used as a control for the in situ hybridization experiments. Unincorporated nucleotides were removed by G50 Sephadex (Pharmacia®) columns.

Ribonuclease Protection Assays

Total cellular RNA was prepared from various tissues of an adult male Sprague-Dawley rat according to standard methods. Assays were carried out using 15 ug of total RNA from each tissue source essentially as described by Zinn et al (1983)[CITATION]. Protected fragments were electrophoresed on a denaturing 5% polyacrylamide gel. The integrity of the RNA was ascertained by protection assay using 32P labeled antisense RNA transcribed from mouse β2-microglobulin cDNA. RNA selection procedure RNA selection procedure The RNA selection process was done according to the method described by Tsai et al (1991). Briefly, an oligodeoxynucleotide containing a T7 promoter sequence (T7Univ) at one end, followed by 25 degenerate nucleotides and then a reverse universal primer sequence (RevUniv) at the other end was used in a PCR reaction (1 min. 94, 1 min. 50, 2 min. 72 in 10 mM Tris-HCl (pH 8.3), 50 mM KCl, 1.5 mM $MgCl_2$, 0.01% gelatin, 0.1 mg of T7Univ and RevUniv primers, 200 mm dNTPs and 2.5 U of Tag DNA polymerase) to create double stranded template for transcription. RNA was synthesized using T7 polymerase using standard methods (Maniatis, 1990).

In binding conditions described previously (Query et al, 1989), the degenerate pool of RNA was then incubated with g10-Hel-N1 fusion protein which had been prebound to protein-A beads (Sigma) using the g10 antibody. The beads were subsequently washed 5 times with NT2 buffer, and the immunoprecipitated RNA was then phenol extracted and ethanol precipitated in the presence of 10 ug of carrier tRNA (Sigma®). The RNA was resuspended in 10 ul of doubly distilled water, and 3 ul was used for PCR amplification under conditions described above. The T7 and RevUniv primers had Bam-H1 restriction sites incorporated in the 5' ends such that any multimer products were reduced to monomers with Bam-H1 digestion. The same process was then carried out two more times. After the final PCR amplification and Bam-H1 digestion, the product was subcloned into pGEM-3Zf(+) and sequenced.

Plasmids and mRNA transcripts

The 3' end of the GM-CSF gene (240 bp fragment between Nco I and Eco RI cleavage sites) inserted into the polylinker, pGem3 containing the 3' end of the human c-fos gene (250 bp RsaI-Tth1111) inserted into the Hinc II site, and pGem3 containing the NsiI-AflIII fragment of the 3' end of the human c-myc gene were used. The plasmids were linearized as follows: GM-CSF in PSP64 was cut at BglII and transcribed with Sp6 RNA polymerase; pGEM 2 containing c-fos was linearized with Kpn 1 and transcribed with T7 RNA polymerase; pGEM3 containing c-myc DNA was linearized with BamHI and transcribed with Sp6 RNA polymerase.

Linearized plasmid DNA was transcribed with SP6 RNA polymerase for c-myc and GM-CSF, or T7 RNA polymerase for c-fos. These reactions were carried out in the presence of 1.25mm ATP, CTP, GTP; 0.75 mm UTP, and 5ul of 1u Ci/ul 32P UTP.

RNA Binding to Hel-N1

For each binding reaction 4 mg of Protein A beads were washed three times in NT2 Buffer (150 mm NaCl, 50 mm Tris—HCl pH 7.4, and 0.05% NP40). 5 ul of rabbit anti-g10 antibody, or 20 ul of human serum, was incubated with Protein A for 10 minutes on ice and washed three times with NT2 buffer. 35 ul of Hel-N1 *E. coli* extract was then added and incubated for ten minutes on ice and washed three times with NT2 buffer. After the final wash, the protein complex was resuspended in 0.1 ml of RNA Binding Buffer and equimolar amounts of labeled transcripts were added.

After a 5 min. incubation at room temperature, the binding reaction was washed five times with NT2 buffer and resuspended in 0.1 ml of NT2 buffer. 0.1 ml of the supernatant from the first wash was saved and treated identically as the bound pellet. 0.1 ml of diethyl pyrocarbonate treated water was added as well as 13 ul of 5M NaCl and 1 ul of 10 mg/ml of tRNA. The reactions were PCI extracted and EtOH precipitated. The pelleted RNA was run on a 6% urea polyacrylamide gel.

UV Cross Linking

Hela cell nuclear extract was prepared as described by Dignam (1983) and label transfer from RNA to protein was carried out as described by Wilusz et al, *Cell* (1988) 52:221–228. 500,000 cpm of labeled transcripts were incubated with 5 ug of nuclear extract in a total reaction volume of 10 ul. The reaction was performed in a microtiter plate and irradiated for 10 minutes on ice. RNase A was added for a final concentration of 1 mg/ml and incubated for 15 minutes at 37° C. The reactions were mixed with Laemmli buffer and run on a 10% SDS polyacrylamide gel.

Hel-N1 crosslinking was carried out as above, except that the protein was dissolved in a uv cross-linking buffer (20mm Hepes, 1 mm $MgCl_2$, 60 mm KCl 10% glycerol). Competition experiments included 5 ug of Hela cell nuclear extract in the presence of increasing amounts of Hel-N1 maintaining a total reaction volume of 10ul.

Cellular Growth

NIH 3T3 cells where transfected with a pBC vector derived from the CMV promoter containing DNA expression RNA binding domain 3 (RBD3) of Hel-N1 using the calcium phosphate method. Cells were co-transfected with a plasmid encoding resistance to neomycin and colonies were selected with neomycin in the growth medium. After approximately three weeks of selection cells were examined by immunoflorescents and found to express RBD3(−), while control cells transfected with neomycin resistance alone (+) did not express RBD3. Cells were counted at passage and planted on culture plates for determination of growth rate. At days 1, 2 and 3 a plate of each was sacrificed and the cell numbers determined. It was readily evident that those cells expressing RBD3 entered into rapid proliferation, while the control cells grew at the same rate as normal 3T3 cells.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for inhibiting cellular growth, comprising causing a cell to express, in vitro, a polypeptide having the whole amino acid sequence of Hel-N1 set forth in FIG. 1.

2. The method of claim 1, comprising administering DNA encoding said polypeptide to said cell in a manner permitting for expression of said polypeptide in said cell.

3. The method of claim 1, comprising administering RNA encoding said polypeptide to said cell in a manner permitting for expression of said polypeptide in said cell.

4. The method of claim 2, comprising using liposome-mediated delivery or retrovirus-mediated delivery of said DNA to said cell.

5. The method of claim 3, comprising using liposome-mediated delivery or retrovirus-mediated delivery of said RNA to said cell.

* * * * *